(12) United States Patent
Brundidge

(10) Patent No.: US 6,708,347 B2
(45) Date of Patent: Mar. 23, 2004

(54) HEAT SHIELD FOR HAIR DRYER

(76) Inventor: Jackie L. Brundidge, 19414 Ridgewood Rd., Warrensville Hts., OH (US) 44122

( * ) Notice: Subject to any disclaimer, the term of this patent is extended or adjusted under 35 U.S.C. 154(b) by 0 days.

(21) Appl. No.: 10/102,305

(22) Filed: Mar. 19, 2002

(65) Prior Publication Data

US 2002/0138894 A1 Oct. 3, 2002

Related U.S. Application Data

(60) Provisional application No. 60/279,590, filed on Mar. 29, 2001.

(51) Int. Cl.[7] ................................. A42B 1/18
(52) U.S. Cl. ..................... 2/174; 2/12; 2/209
(58) Field of Search ................. 2/12, 15, 174, 2/209, 171, 448

(56) References Cited

U.S. PATENT DOCUMENTS

| | | | | |
|---|---|---|---|---|
| 1,621,629 A | * | 3/1927 | Dawson | 2/448 |
| 2,112,916 A | * | 4/1938 | Linden | 2/174 |
| 2,424,352 A | * | 7/1947 | Conjurske | 2/174 |
| 2,696,008 A | * | 12/1954 | Penman et al. | 72/203 |
| 2,729,823 A | * | 1/1956 | Foster | 106/433 |
| 3,611,442 A | * | 10/1971 | Yazaki | 2/174 |
| D250,296 S | | 11/1978 | Breland | |
| 4,133,052 A | | 1/1979 | Hodgman et al. | |
| 4,704,744 A | | 11/1987 | Myers | |
| D315,224 S | | 3/1991 | Curlee | |

* cited by examiner

Primary Examiner—Katherine Moran
(74) Attorney, Agent, or Firm—Tarolli, Sundheim, Covell & Tummino L.L.P.

(57) ABSTRACT

Protective headwear for use under a hair dryer includes a strap which extends across the forehead of the wearer. A visor is attached to the bottom of the strap and covers and protects the eyes and nose of the wearer. A pair of earpieces are connected to opposite sides of the forehead strap by means of elastic connectors. Each earpiece has a first section and a bendable end section which extends around an ear of the wearer. Flaps are attached to and hang down from the first section to cover the ears. The forehead strap may be elastic and extendable, and the visor may be fan shaped.

5 Claims, 2 Drawing Sheets

HEAT SHIELD FOR HAIR DRYER

RELATED APPLICATION

This application claims benefit of provisional patent application Ser. No. 60/279,590 filed Mar. 29, 2001.

TECHNICAL FIELD

The present invention relates to improved protective headwear for use with a hair dryer, particularly with a hood hair dryer of the type used in a beauty salon.

BACKGROUND OF THE INVENTION

Patrons of beauty salons often feel discomfort when under a hair dryer. Complaints frequently focus on excessive heat on the forehead and on ears, eyes and nose discomfort.

Utility U.S. Pat. No. 4,133,052 discloses protective headgear having a transparent visor to cover the wearer's eyes and nose, earflaps to cover the ears, and an insulated middle segment which extends across the forehead. Tie members connected to the middle segment extend around the back of the head to hold the headgear on the head of the wearer. The headgear is said to protect the wearer from heat-induced discomfort which otherwise might be caused by a hair dryer. The device is reusable and thus is not disposable.

Examples of other protective headgear are shown in design Pats. Nos. 250,296 and 315,224, and in Utility Pat. No. 4,704,744.

SUMMARY OF THE INVENTION

The present invention relates to protective headwear for use under a hair dryer. The headwear is disposable. The headwear comprises a strap which extends across the forehead of the wearer. A visor is attached to the bottom of the strap and covers and protects the eyes and nose of the wearer. The visor is made of a rigid material such as plastic or cardboard, and is curved to conform to the forehead of the wearer. A pair of earpieces are connected to opposite sides of the forehead strap by means of elastic connectors. Each earpiece has an elongated rigid inner section and a bendable end section which extends around an ear of the wearer. Flaps are attached to and hang down from the rigid inner section to cover the ears. The bendable end sections are readily bent to conform to the ears of the wearer and hold the headwear on the wearer similar to the earpieces of a pair of glasses. As the earpieces are connected to the forehead strap by elastic connectors, the headwear can easily be adapted to fit the head of any wearer. This makes the headwear of the present invention disposable. All of the components of the headwear are readily available commercial materials, and the assembly of the headwear is simple, so that the headwear of the present invention is inexpensive enough that it is disposable for this reason as well.

In an embodiment of the present invention, the elastic attached to the earpieces extends all the way across the forehead of the wearer from earpiece to earpiece. In the area of the visor, the elastic is covered with fabric to protect the wearer from heat absorbed by the elastic. The visor is fan shaped, so that when the headgear is placed over a very wide head, the visor expands as well as the elastic between the earpieces.

BRIEF DESCRIPTION OF THE DRAWINGS

The invention and advantages thereof will become more apparent from the following detailed description with reference to the accompanying drawings in which.

DETAILED DESCRIPTION OF THE INVENTION

Figure 1:
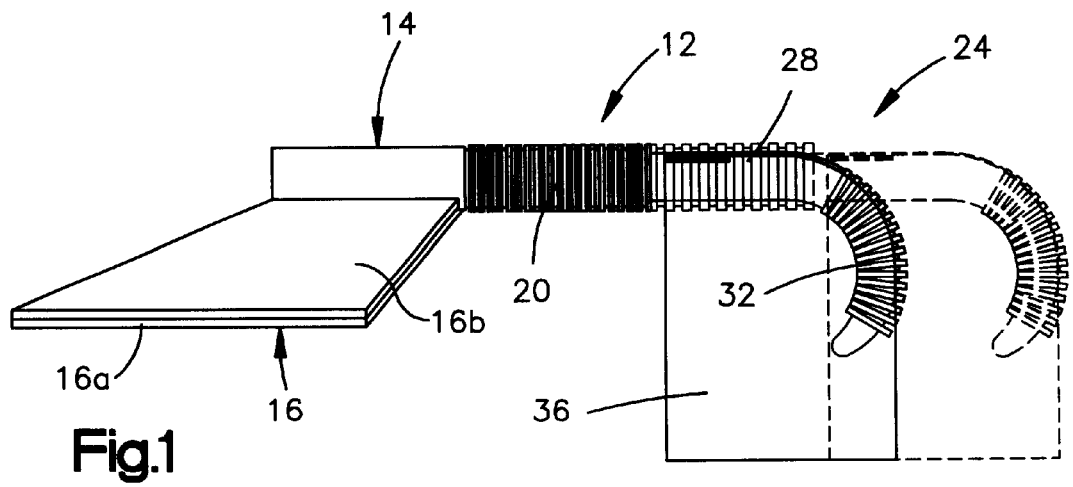
FIG. 1 is a side elevation view of a protective headwear of the present invention.
Figure 2:
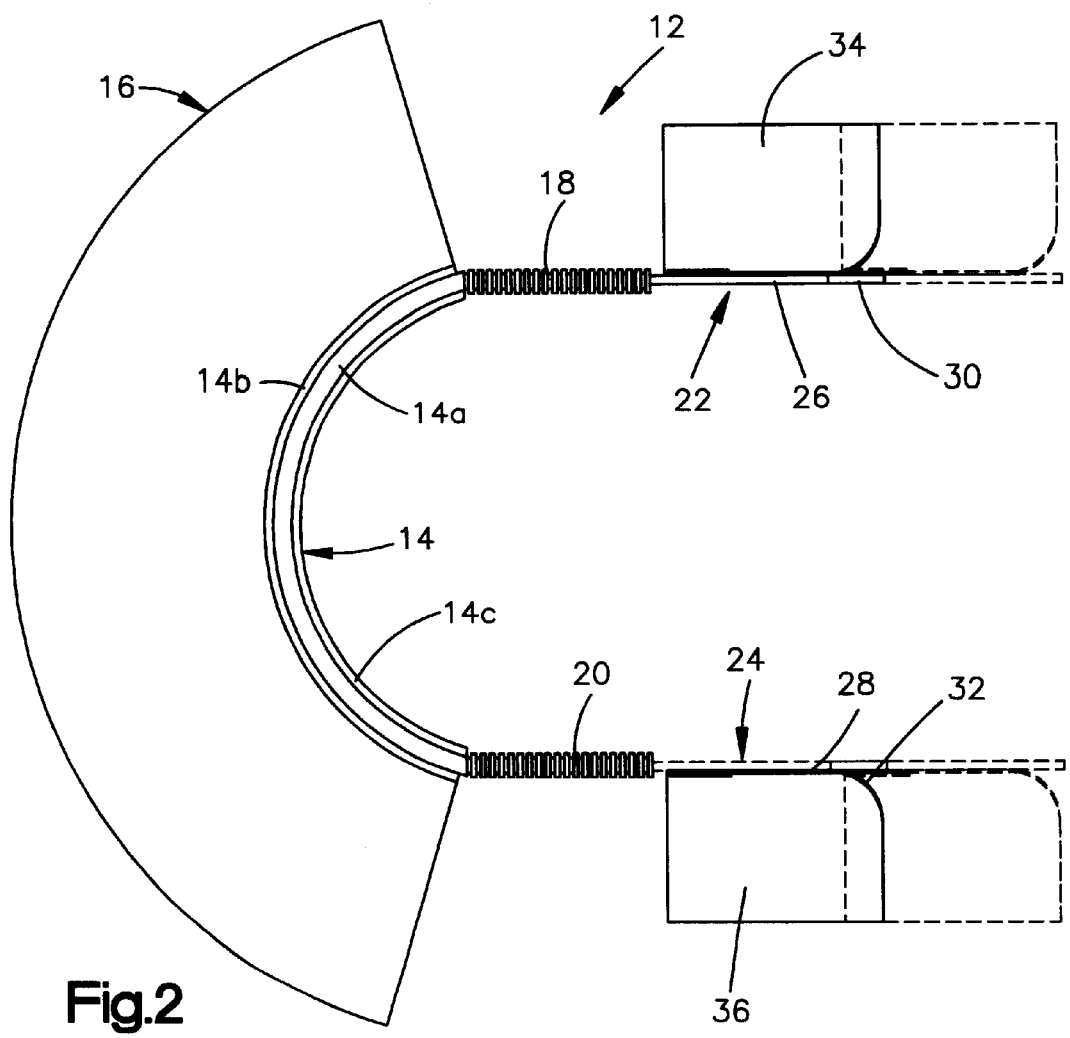
FIG. 2 is a plan view of the protective headwear of FIG. 1.

Referring to FIGS. 1 and 2, the protective headwear 12 of the present invention comprises a strap 14 which extends across the forehead of the wearer. The strap 14 is relatively narrow in width (vertical dimension), preferably no more than about two inches, and preferably about one-half inch. The strap 14 is preferably of a height that it does not reach up to the wearer's hairline, but only rests on the skin of the forehead. The strap 14 is made of a flexible material so that it seals against the forehead.

Specifically, the strap 14 is made of a base 14a that may be polypropylene, for example, or another lightweight material strong enough to serve as a support. The strap 14 has a layer 14b on its outwardly facing surface that is made from a heat resistant and fire retardant material, such as Nomex brand material or another brand. The strap 14 has a layer 14c on its inwardly facing surface that is made from a material comfortable to the wearer, such as cotton or terry cloth. Various materials can be used.

The length of the strap 14 is enough that it extends across the width of the forehead of the wearer. Here also, the length of the strap 14 is not critical, as long as it extends more or less the full distance across the forehead of the wearer.

The strap 14 supports a visor 16. The visor 16 is relatively rigid, and is made of a base material 16a such as plastic or cardboard. It is preferably covered on its outward facing surface with a layer 16b of heat resistant and fire retardant material, such as Nomex brand material or another brand. The fire retardant layer 16b may be a separate material layer or may be a sprayed on coating. The strap 14 has a layer 14c on its inwardly facing surface that is made from a material comfortable to the wearer, such as cotton or terry cloth. Various materials can be used, for example, a woven fabric, nylon, etc.

The visor 16 is attached to the strap 14, for instance by sewing. The visor 16 is preshaped, similar to the visor of a baseball cap, to more or less conform to the shape of the forehead of a wearer. Despite this, the strap 14 preferably allows the headwear 12 to seal against the forehead of the wearer. The visor 16 extends downwardly but primarily outwardly from the strap 14 about four inches, more or less, to protect the eyes and nose of the wearer from the heat of the hair dryer. The visor 16 does not extend downward like a mask to actually cover the eyes and nose.

Connectors 18 and 20 are attached to opposite ends of the strap 14. The connectors 18 and 20 are made of an elastic material, for instance an elastic fabric or bungee material. Such elastic materials are commercially available. The connectors 18 and 20, because they are elastic, are longitudinally (front to back) extensible, as can be seen from a comparison of FIGS. 1 and 2. It should be understood that the present invention encompasses connectors that are not elastic, also.

Earpieces 22 and 24 are attached to the connectors 18 and 20, respectively. Preferably, the ear pieces 22 and 24 have relatively rigid straight portions 26 and 28 which are attached to the connectors 18 and 20, respectively, and bendable end portions 30 and 32 which can be curved to conform to the ears of the wearer, that is, curved to have a shape generally similar to the ear pieces of a pair of glasses. Preferably the earpieces are made of plastic. An example of a bendable material that would be useable in the earpieces of the present invention is a plastic straw of the type often dispensed with the purchase of a soft drink. The bendable portions 30 and 32 are corrugated making them bendable and at the same time providing memory so that the portions 30 and 32 retain the shape to which they are bent.

Ear covers 34 and 36 are attached to the straight portions 26 and 28. The ear covers 34 and 36 are generally rectangular pieces which hang downwardly from the straight portions 26 and 28 of the earpieces 22 and 24. The size and shape of the ear covers 34 and 36 is not critical, so long as they are large enough to cover at least substantially the ears of the wearer and protect the ears from the heat of the hair dryer. Preferably the ear covers 34 and 36 are made from the same combination of materials as the strap 14. The ear covers 34 and 36 can be attached to the earpieces 22 and 24 by sewing or other means. The ear covers are preferably stiff, not flexible.

Advantages of the present invention should now be apparent. Primarily, the protective headwear 12 of the present invention is easily adapted to fit the head of any wearer making it disposable. The elastic connectors 18 and 20 are made sufficiently elastic that the bendable end portions 30 and 32 fit securely over the ears of the wearer without causing the wearer any discomfort from excessive tension in the connectors 18 and 20. The extensibility of the elastic connectors is illustrated in FIGS. 1 and 2 by the dashed lines for earpieces 22 and 24. The use of a bendable plastic with memory for the portions 30 and 32 makes the headwear 12 even more adjustable for different shaped heads. At the same time, the design of the headwear is sufficiently simple that it can be made inexpensively of inexpensive materials readily available in the marketplace. This also makes the headwear of the present invention disposable.

Figure 3:
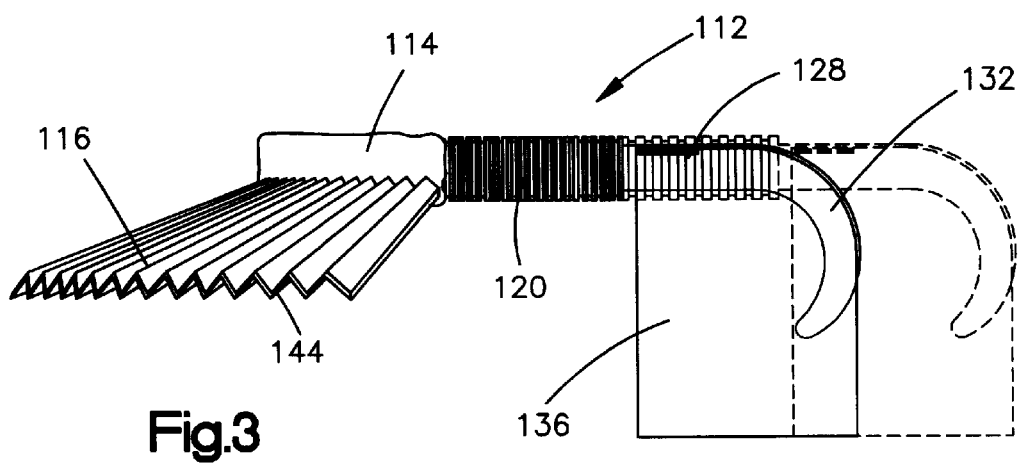
FIG. 3 is a side elevation view of a protective headwear in accordance with an embodiment of the present invention.
Figure 4:
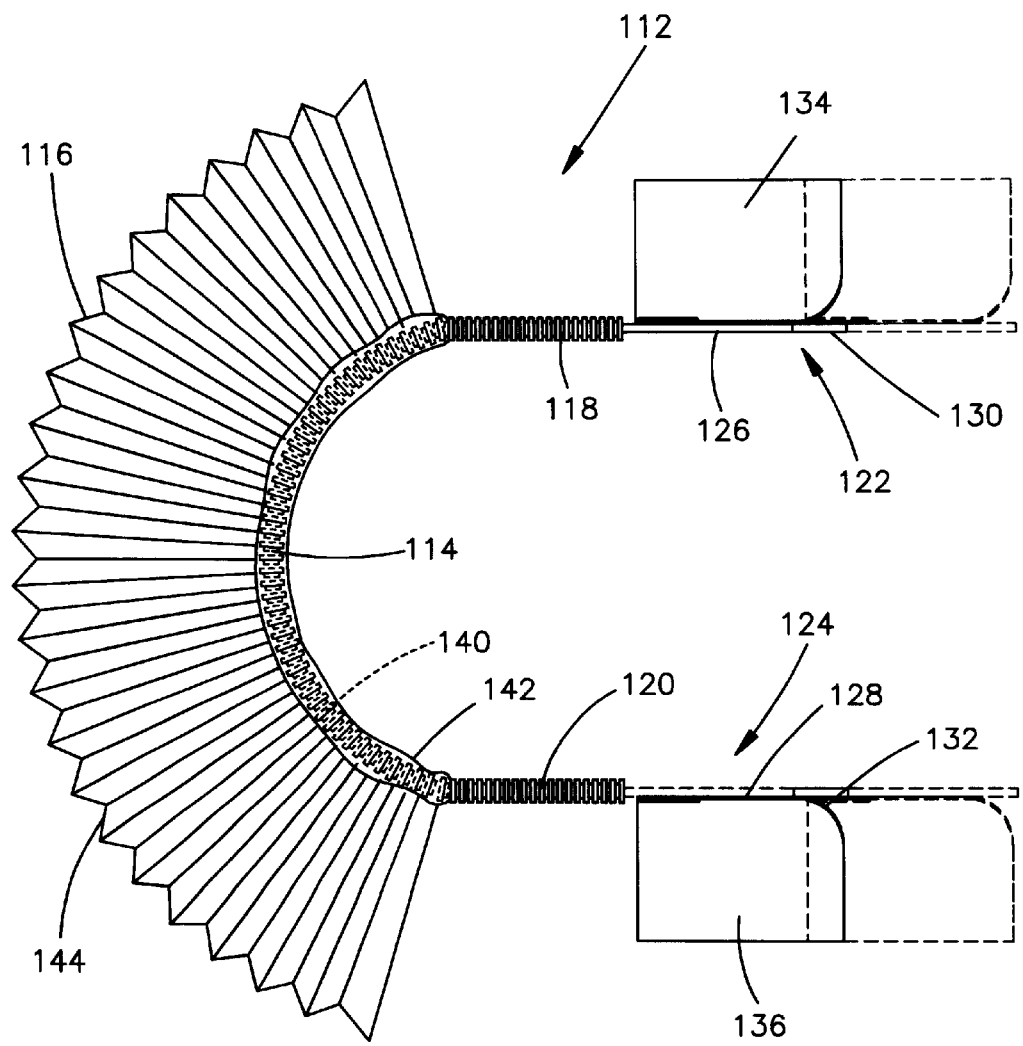
FIG. 4 is a plan view of the protective headwear of FIG. 3.

A second embodiment of the present invention is shown in FIGS. 3 and 4. In this embodiment, the headwear 112 comprises a strap 114, a visor 116, connectors 118 and 120, and earpieces 122 and 124, as in the embodiment of FIGS. 1 and 2. The earpieces have a relatively straight, rigid portion 126,128 and a bendable portion 130,132 having memory so that the bendable portion 130,132 retains the shape to which it is bent. Earflaps 134,136 drape from the rigid portion 126,128. The elasticity in the connectors 118 and 120 allows the headwear to be adjusted to any shaped head. In this embodiment of the present invention, the strap 114 comprises an inner elastic and stretchable member 140, covered loosely by a fabric member 142. The elastic member 140 allows the strap 114 to be stretched to conform to very wide heads, making the embodiment of FIGS. 3 and 4 even more adaptable to different shaped heads, and thus even more readily disposable. To facilitate adaptability to different shaped heads, the visor 116 is fan shaped having corrugations 144 which allow the visor to be fanned out or widened as with a conventional fan when the strap 114 is stretched. The construction of the visor 116 can be the same as that of a conventional fan.

From the foregoing, variations and modifications of the invention will be apparent to those skilled in the art. Such variations and modifications of the invention within the skill of the art are intended to be covered by the claims appended hereto.

Having described the invention, I claim:

1. A disposable protective headwear for use with a hair dryer, said protective headwear comprising:
    (a) a forehead strap extendable across the forehead of a wearer, said forehead strap having an outer surface formed of a heat resistant material which is capable of withstanding heat from the hair dryer;
    (b) a visor attached to the strap and adapted to extend outward over the eyes and nose of the wearer, said visor having an upper side surface formed of a heat resistant material which is capable of withstanding heat from the hair dryer;
    (c) a pair of ear pieces;
    (d) connectors attaching the ear pieces to opposite ends of the forehead strap, said connectors being resiliently extendable from a first length to a second length to enable said ear pieces to be positioned at a desired distance from said visor, each one of the ear pieces includes
        (i) a first portion attached to the connectors; and
        (ii) a bendable end portion extending from the first portion, the bendable end portion which is bendable around the ear of the wearer and retains the shape to which it is bent; and
    (e) an ear cover extending from the first portion to protect an ear of a wearer of the protective headwear from heat from the hair dryer.

2. A protective headwear as set forth in claim 1, wherein the forehead strap is elastic and extendable.

3. A protective headwear as set forth in claim 2, wherein the visor is fan shaped comprising corrugations allowing the visor to be widened with extension of the forehead strap.

4. A protective headwear as set forth in claim 1, wherein said forehead strap includes an inner layer formed of cotton and an outer layer formed of a heat resistant material.

5. A protective headwear as set forth in claim 1, wherein said visor includes a base layer and a layer of heat resistant material overlying said base layer.

* * * * *